United States Patent [19]
Harland et al.

[11] Patent Number: 6,008,339
[45] Date of Patent: Dec. 28, 1999

[54] NUCLEIC ACIDS ENCODING A NEURAL TISSUE AFFECTING FACTOR

[75] Inventors: Richard M. Harland, Berkeley; William C. Smith, Oakland, both of Calif.

[73] Assignee: The Regents of the University of California, Oakland, Calif.

[21] Appl. No.: 08/517,802

[22] Filed: Aug. 22, 1995

Related U.S. Application Data

[63] Continuation of application No. 08/117,370, Sep. 3, 1993, abandoned.

[51] Int. Cl.[6] .............................. C12N 15/18; C12N 1/21; C12N 15/63; C12N 15/85
[52] U.S. Cl. ................. 536/23.51; 536/23.1; 435/320.1; 435/69.4; 435/252.3; 435/325
[58] Field of Search .................... 536/23.1, 24.3, 536/23.51; 435/320.1, 252.3, 69.1, 69.4, 325

[56] References Cited

U.S. PATENT DOCUMENTS

| | | | |
|---|---|---|---|
| 4,857,637 | 8/1989 | Hammonds et al. | 530/403 |
| 4,933,294 | 6/1990 | Waterfield et al. | 436/501 |
| 5,030,576 | 7/1991 | Dull et al. | 435/69.7 |
| 5,177,197 | 1/1993 | Kanzaki et al. | 435/240.2 |
| 5,229,500 | 7/1993 | Barde et al. | 530/399 |

FOREIGN PATENT DOCUMENTS

| | | |
|---|---|---|
| 93/09228 | 5/1993 | WIPO . |
| 93/09229 | 5/1993 | WIPO . |

OTHER PUBLICATIONS

Basler et al., "Control of Cell Pattern in the Neural Tube: Regulation of Cell Differentiation by dorsalin–1, a Novel TGFβ Family Member," *Cell*, 73, (May 21, 1993), pp. 687–702.

Lin et al., "GDNF: A Glial Cell Line–Derived Neurotrophic Factor for Midbrain Dopaminergic Neurons," *Science*, 260 (May 21, 1993), pp. 1130–1132.

Weiss, Rick, "Promising Protein for Parkinson's," *Science*, 260 (May 21, 1993), pp. 1072–1073.

Rudinger In "Peptide Hormones" (Jun. 1976) ed. J.A. Parsons, University Park Press, Baltimore, pp. 1–7.

Celeste et al *Proc. Natl Acad Sci USA* 84:9843–47 (1990).

denDunnen et al. *Gene* 78 : 201–213 (1989).

Kitchens et al. *J of Neurobiol* 25(7) : 797–877 (1994).

Nishamatsu et al *Biochem Biophys Res Com* 186(3): 1487–95 (1992).

Padgett et al. *Proc Natl Acad Sci USA* 90: 2905–09 (1993).

Shimell et al. *Cell* 67 : 469–481 (1991).

Zhou et al. *Nature* 361 : 543–47 (1993).

*Primary Examiner*—Paula K. Hutzell
*Assistant Examiner*—Robert C. Hayes
*Attorney, Agent, or Firm*—Majestic, Parsons, Siebert & Hsue

[57] ABSTRACT

A functional peptide is encoded by SEQ ID NO:1. This peptide is capable of inducing dorsal and neural tissue development in vertebrates. The peptide is a member of the TGF-β superfamily, and can be prepared in therapeutic applications to treat congenital conditions or degenerative disorders of the nervous system and in compositions useful for inducing growth of bone.

4 Claims, 1 Drawing Sheet

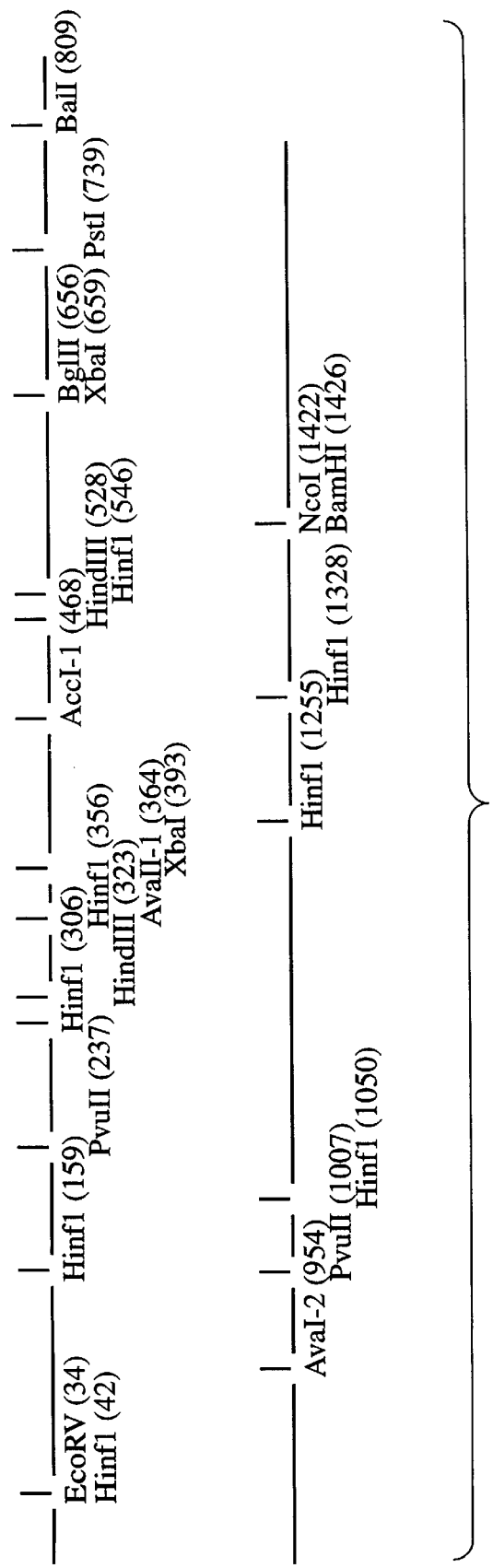
FIG._1

NUCLEIC ACIDS ENCODING A NEURAL TISSUE AFFECTING FACTOR

This is a continuation of application Ser. No. 08/117,370, filed Sep. 3, 1993 (abandoned).

FIELD OF THE INVENTION

The invention generally relates to growth factors and neurotrophic factors, and more particularly to a growth factor with dorsal growth (and neural tissue) inducing activity, to complexes and compositions including the factor, and to DNA or RNA coding sequences for the factor.

BACKGROUND OF THE INVENTION

Growth factors are substances, such as polypeptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines and trophic factors. Among growth, or neurotrophic, factors presently known are the transforming growth factors (TGF-α, TGF-β, TGF-γ)]. Transforming growth factor-β appears to elicit a variety of responses in many different cell types.

Receptors that affect growth (that is, receptors for growth-associated ligands) are proteins found associated with cell surfaces that specifically bind their growth factors as ligands. Growth factor receptors are utilized in various clinical and diagnostic applications, such as are described by: U.S. Pat. No. 4,857,637, issued Aug. 15, 1989, inventors Hammonds et al. (a method for immunizing an animal against its growth hormone receptor through use of vaccinating with antibodies); U.S. Pat. No. 4,933,294, issued Jun. 12, 1990, inventors Waterfield et al. (studies of structural alterations of the human EGF receptor and its gene and a relationship in tumorigenesis for assays and therapies involving the human EGF receptor); and U.S. Pat. No. 5,030,576, issued Jul. 9, 1991, inventors Dull et al. (use of receptor growth factors, in designing drugs by the pharmaceutical industry, and use of a receptor hybrid for screening drug purposes). DNA encoding several different receptors for TGF-β has recently been described by Lin et al., PCT application WO93/09228, published May 13, 1993. The availability of the TGF-β receptors will facilitate further assessments of TGF-β functions.

Kanzaki et al., U.S. Pat. No. 5,177,197, issued Jan. 5, 1993, describe a DNA which expresses a protein known as platelet TGF-β 1-BP. The protein is said to be useful for producing anti-sera in order to identify complexes containing the binding protein, as well as in formation of labeled probes.

Widespread neuronal cell death accompanies normal development of the central and peripheral nervous systems. Studies of peripheral target tissues during development have shown that neuronal cell death results from the competition among neurons for limiting amounts of survivor factors ("neurotrophic factors"). The earliest identified of these, nerve growth factor ("NGF"), is the most fully characterized and has been shown to be essential for the survival of sympathetic and neural crest-derived sensory neurons during early development of both chick and rat. Barde et al., U.S. Pat. No. 5,229,500, issued Jul. 20, 1993, describe nucleic acid sequences encoding brain derived neurotrophic factor ("BDNF"), as well as the BDNF protein. BDNF is suggested for treating Parkinson's Disease and Alzheimer's Disease. Additional uses (quite recently performed successfully) are for the identification of homologous regions between BDNF and NGF so as to identify and isolate additional members of the NGF family, and also to generate immunogen by antibodies directed toward BDNF or fragments.

Among the exciting new possibilities for neurotrophic factors are applications involving neural tissue, such as to prevent degradation of dopaminergic neurons in treating Parkinson's disease. One of the most recently isolated new proteins appears selectively to promote survival of the neurons that secrete the neurotransmitter dopamine. Lin et al., Science, 260, pp. 1130–1132 (1993). This new neurotropic factor is a glial derived neurotrophic factor and is said to be distantly related to the TGF-β superfamily.

Many members of the TGF-β super family have been characterized. For example, Basler et al. have graphically represented the sequence relationship between members of the TGF-β superfamily. Cell, 73, pp. 687–702 (1993).

Also among TGF-β members are the bone morphogenetic proteins (BMP). The BMPs have been indicated as useful in wound healing, tissue repair, and to induce cartilage and/or bone growth. For example, PCT Application 9309229, inventors Israel and Wolfman, published May 13, 1993, describes uses of proteins with bone stimulating activity such as bone fracture healing and possibly the treatment of periodontal disease and other tooth repair processes.

Thus, growth factors, their receptors, and DNA or RNA coding sequences therefore and fragments thereof are useful in a number of therapeutic, clinical, research, diagnostic, and drug design applications.

SUMMARY OF THE INVENTION

In one aspect of the present invention, a peptide that can be in substantially purified form is encoded by SEQ ID NO: 1. SEQ ID NO:1 codes for a functional polypeptide that we have designated "dor3," which is capable of inducing dorsal (and neural tissue) development in vertebrates when expressed, and whose deduced amino acid sequence is illustrated by SEQ ID NO:3. Since peptides of the invention induce dorsal and neural tissue growth in vertebrates, they can be prepared in physiologically active form for a number of therapeutic, clinical, and diagnostic applications.

The inventive peptide is a member of the TGF-β superfamily and is related to the BMPs. Compositions of the invention include osteogenically effective amounts of Dor3 in pharmaceutically acceptable excipients or carriers or admixed with biomaterials such as a calcium containing composition.

In another aspect of the present invention an oligonucleotide, such as cDNA, is provided having substantial similarity to (or being the same as) SEQ ID NO:1. This oligonucleotide can be single or double stranded, be formed of DNA or RNA bases, and can be in the antisense direction, as illustrated by SEQ ID NO:2.

Dor3 or fragments thereof (which also may be synthesized by in vitro methods) may be fused (by recombinant expression or in vitro covalent methods) to an immunogenic polypeptide and this, in turn, may be used to immunize an animal in order to raise antibodies against a dor3 epitope. Anti-dor3 is recoverable from the serum of immunized animals. Alternatively, monoclonal antibodies may be prepared from cells to the immunized animal in conventional fashion. Antibodies identified by routine screening will bind to dor3 but will not substantially cross-react with other members of the TGF-β family of growth factor. Immobilized anti-dor3 antibodies are useful particularly in the diagnosis (in vitro or in vivo) or purification of dor3.

Substitutional, deletional, or insertional mutants of dor3 may be prepared by in vitro or recombinant methods and screened for immuno-crossreactivity with dor3 and for dor3 antagonist or agonist activity.

Dor3 also may be derivatized in vitro in order to prepare immobilized dor3 and labelled dor3, particularly for purposes of diagnosis of insufficiencies of dor3 or its antibodies, or for affinity purification of dor3 antibodies.

BRIEF DESCRIPTION OF THE DRAWINGS

FIG. 1 illustrates a restriction enzyme map for an oligonucleotide of the invention.

DESCRIPTION OF THE PREFERRED EMBODIMENTS

We have discovered a novel neurotrophic factor that induces dorsal development in vertebrates, that is a member of the TGBβ superfamily, and that we have named "dor3." When referring to dor3, the present invention also contemplates the use of fragments, derivatives, agonists, or antagonists of dor3 molecules.

We have cloned cDNA for dor3. The dor3 cDNA contains a reading frame encoding a 401 residue, 46 kDa precursor protein with a hydrophobic amino-terminal sequence. By similarity to the BMP family of proteins, the sequence predicts a mature, carboxy-terminal, processed product of 14 kDa.

Dor3 nucleic acids, or oligonucleotides, encode a dor3 polypeptide or hybridize to such DNA and remain stably bound to it under stringent conditions and are greater than about 10 bases in length. By "stringent conditions" we mean those which (1) employ low ionic strength and high temperature for washing, for example, 0.15 M NaCl/0.015 M sodium citrate/0.1% NaDodSo$_4$ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

By "substantial similarity," when we are referring to a nucleotide sequence, is meant cross hybridization of sequences under conditions of moderate stringency using a probe greater than about 100 nucleotides long at 30° C. in a standard buffer (Wahl et al., *PNAS*, 76, 3683) and washes at 37° C. in 300 mM NaCl, 30 mM sodium citrate, 0.2% SDS at pH 7. Alternatively, one is able to isolate, by polymerase chain reaction, a fragment of DNA coding for dor3 or dor3 family members when using primers of degenerate sequence.

By "substantial similarity" when reference is made to proteins is that dor3 from different species, or dor3 family members within a species, have preserved positions of cysteine residues in at least 90% of positions throughout the protein. To illustrate that dor3 is a new member of the BMP family, we have compared dor3 to the protein databases using the BLAST program (National Library of Medicine). What we believe to be the closest relative, another BMP family member called nodal, scores only 33% identity overall and only 52% identity in the C-terminal region. By contrast, as above noted, we predict that the human dor3 will be greater than 60% identical overall and 90% identical in the C-terminal region.

Similarity at the protein level includes an ability of a subject protein to compete with dor3 for binding to receptors and some (but not all) monoclonal antibodies raised against dor3 epitopes.

Like the members of the BMP family, the sequence of the mature form of dor3 and dor3 related polypeptides will be identical in at least 90% of positions. Thus, based on comparisons of Xenopus BMP-2 with human BMP-2, Xenopus BMP-4 with human BMP-4, and Xenopus BMP-7 with human BMP-7, we expect that there will be a sequence identity of greater than 60% over the entire coding sequence, and an identity of greater than 90% over the C-terminal 100 amino acid residues. Our comparisons to BMP proteins were carried out using the "bestfit" program of the Genetics Computer Group, (1991). The comparison with Xenopus BMP-2 showed a percent identity of 74.6%, with human BMP-2 showed a percent identity of 83%, and with human BMP-7 showed a percent identity of 61.6%.

The cloned cDNA for dor3 (derived from frog) is designated herein as SEQ ID NO:1. We have used RNA transcripts from the SEQ ID NO:1 clone to rescue embryos and return them to substantially normal development when the dor3 RNA is injected into ventralized embryos.

When using nucleotide sequences coding for part or all of dor3 in accordance with this invention, the length of the sequence should be at least sufficient in size to be capable of hybridizing with endogenous mRNA for the vertebrate's own dor3. Typically, sufficient sequence size (for example, for use as diagnostic probes) will be about 15 consecutive bases (DNA or RNA). In some diagnostic and therapeutic applications, one may wish to use nucleotide dor3 coding sequences (analogous to all or a portion of SEQ ID NO:1) in the anti-sense direction.

Although dor3 transcript is not localized in the oocyte and cleavage stage embryo, zygotic transcripts are initially restricted to the presumptive dorsal mesoderm, and reach their highest levels at the gastrula stage in the dorsal lip of the blastopore (Spemann's organizer). In the neurula, dor3 is transcribed in the notochord and prechordal mesoderm.

Without being bound by theory, we have formulated hypotheses about the embryological effects of dor3 based on where it is expressed, and on the effects of RNA injection in embryos. Since dor3 is expressed in the Spemann organizer, we believe dor3 to be a mediator of the effects of the Spemann organizer, namely neural induction and dorsalization of the mesoderm.

A number of applications for dor3 are suggested from its properties.

The dor3 cDNA should be useful as a diagnostic tool (such as through use of antibodies in assays for proteins in cell lines or use of oligonucleotides as primers in a PCR test to amplify those with sequence similarities to the oligonucleotide primer, and to see how much dor3 is present).

Dor3, of course, provides the key to isolate its receptor. Since many receptors mutate to cellular oncogenes, the dor3 receptor should prove useful as a diagnostic probe for certain tumor types. When one views dor3 as a ligand in complexes, then complexes in accordance with the invention include antibody bound to dor3, antibody bound to peptides derived from dor3, dor3 bound to its receptor, or peptides derived from dor3 bound to its receptor. Such complexes of dor3 and its binding protein partners will find uses in a number of applications. Mutant forms of dor3, which are either more potent agonists or antagonists, are also believed to be clinically useful.

Practice of this invention includes use of an oligonucleotide construct comprising a sequence coding for dor3 and for a promoter sequence operatively linked to dor3 in a mammalian, bacterial, or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. The well-known plasmid pBR322 is suitable for most gram negative bacteria, the 2 μ plasmid origin for yeast, and various viral origins (Sv40, polyoma, adenovirus, VSV or BPV) are useful for cloning vectors in mammalian cells.

Expression and cloning vectors should contain a selection gene, also termed a selectable marker. Typically, this is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies.

Examples of suitable selectable markers for mammalian cells are dihydrofolate reductase (DHFR) or thymidine kinase. Such markers enable the identification of cells which were competent to take up the dor3 nuclei acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed. Amplification is the process by which genes in greater demand for the production of a protein critical for growth are reiterated in tandem within the chromosomes of successive generations of recombinant cells. Increased quantities of dor3 can therefor be synthesized from the amplified DNA.

For example, cells transformed with the DHFR selection gene are first identified by culturing all of the transformants in a culture medium which contains methotrexate (Mtx), a competitive antagonist of DHFR. An appropriate host cell in this case is the Chinese hamster ovary (CHO) cell line deficient in DHFR activity, prepared and propagated as described by Urlaub and Chasin, *Proc. Nat. Acad. Sci.*, 77, 4216 (1980). The transformed cells then are exposed to increased levels of Mtx. This leads to the synthesis of multiple copies of the DHFR gene and, concomitantly, multiple copies of other DNA comprising the expression vectors, such as the DNA encoding dor3. Alternatively, host cells transformed by an expression vector comprising DNA sequences encoding dor3 and aminoglycoside 3' phosphotransferase (APH) protein can be selected by cell growth in medium containing an aminoglycosidic antibiotic such as kanamycin or neomycin or G418. Because eukarotic cells do not normally express an endogenous APH activity, genes encoding APH protein, commonly referred to as neo resistant genes, may be used as dominant selectable markers in a wide range of eukaryotic host cells, by which cells transformed by the vector can readily be identified.

Expression vectors, unlike cloning vectors, should contain a promoter which is recognized by the host organism and is operably linked to the dor3 nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters can be operably linked to dor3 encoding DNA by removing them from their gene of origin by restriction enzyme digestion, followed by insertion 5' to the start codon for dor3.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exit then synthetic oligonucleotide adapters or linkers are used in accord with conventional practice.

Transcription of dor3-encoding DNA in mammalian host cells is controlled by promoters obtained from the genomes of viruses such as polyoma, cytomegalovirus, adenovirus, retroviruses, hepatitis-B virus, and most preferably Simian Virus 40 (SV40), or from heterologous mammalian promoters, e.g. the actin promoter. Of course, promoters from the host cell or related species also are useful herein.

As recently noted by Wang et al., *Biotechnol. Prog.*, 9, pp. 355–361 (1993), more than 300 heterologous proteins have been expressed in insect cell baculovirus expression systems. Such systems have several advantages, including the overproduction of functional heterologous proteins owing to proper post-translational modifications and a strong polyhedron promoter, the ease of cell propagation due to the earlier development of mammalian cell cultures, and the minimization of environmental health and safety concern due to host-range limitations of the recombinant virus. These factors suggest this system for large-scale industrial protein production. Thus, dor3 can be expressed in insect host cells by means of baculovirus under the control of a promoter, such as the polyhedron promoter of *Autrographa californica* multiple nucleo polyhedrosis virus.

Expression of dor3 can also be, for example, in *E. coli*, and can be performed using vectors such as a lac UV5 promotor, which may be controlled by the lactose operon repressor. Other vectors include those with a strong ribosome binding site, for example the ribosome binding site of bacteriophage T7. Expression can also be in a high copy number kanamycin resistant pBR322-derived plasmid under the control of a lac UV5 promoter.

Dor3 is believed to find uses as an agent for enhancing the survival or inducing the growth of nerve and muscle cells. It, therefore, is useful in the therapy of congenital conditions or degenerative disorders of the nervous system ("neurodegenerative diseases"), including such diseases as Alzheimer's disease, Parkinson's disease, Huntington's chorea, ALS, peripheral neuropathies, and other conditions characterized by necrosis or loss of neurons, whether central, peripheral, or motorneurons. In addition, it may be useful for treating damaged nerve cells, e.g., nerves damaged by traumatic conditions such as burns and wounds, diabetes, kidney dysfunction, and the toxic effects of chemotherapeutics used to treat cancer and AIDS. It also is useful as a new component of culture media (such media being well known to the art) for use in culturing nerve cells in vitro.

The capacity of dor3 to induce neural tissue may be useful in diseases where neural tissue is formed improperly or incompletely during development. Thus, dor3 and the dor3 gene are also useful in treating congenital malformations, such as anencephaly, or the loss of cerebral hemispheres which results from failure of closure of the anterior neural tube during development.

Therapeutic compositions of this invention will include dor3 in concentrations that depend upon the effective doses required and the modes of administration used. Doses used should be sufficient to achieve circulating plasma concentrations of active ingredient that are efficacious. Effective doses may be extrapolated from dose-response curves derived from in vitro or animal model test systems.

Dor3 also is useful for inducing growth of bone. Thus, osteogenically effective amounts of Dor3 in a pharmaceutically acceptable carrier or excipient can be administered for inducing deposition and maturation of bone at the site. In addition, Dor3 can be admixed with or carried by biomaterials, such as hydroxyapatite for bone generation or repair applications in a method such as is described by U.S. Pat. No. 5,158,934, issued Oct. 27, 1992, U.S. Pat. No. 5,208,219, issued May 4, 1993, by compositions such as described in U.S. Pat. No. 5,178,845, issued Jan. 12, 1993, all incorporated herein by reference. Such bone repair compositions typically include various calcium phosphate mineral component materials such as, for example, hydroxyapatites commercially available under the designations Synthograft, Tricalcium Phosphate, or Periogras. The hydroxyapatite (or tricalcium phosphate) may be prepared by known methods rather than commercially purchased, such as those disclosed by Termine et al., *Arch. Biochem. Biophys.* 140, TP307–325 (1970). Such a material can be supplied as a powder with preferred particle sizes typically in the range of about 100–2,000μ.

Practice of this invention includes preparation and uses of a diagnostic or therapeutic agent comprising a nucleotide sequence, preferably of at least about 15 DNA or RNA bases, analogous to all or a portion of either SEQ ID NO:1 or SEQ ID NO:2 (SEQ ID NO:2 is the non-coding strand of a cDNA clone for dor3). Dor3 preparations are also useful as standards in assays for dor3 and in competitive-type receptor binding assays when labelled with radioiodine, enzymes, fluorophores, spin labels, and the like.

Dor3 may be administered in any pharmacologically acceptable carrier, and depending upon the desired mode of administration may be formulated along with liquid carrier into liposomes, microcapsules, polymers or wax-based and controlled release preparations, or be formulated into tablet, pill, or capsule forms.

Administration may be by any mode of administration known in the art, including but not limited to intravenous, intrathecal, subcutaneous, injection, intranasal, oral, or via an implanted device. Suitable implants include, for example, gel foam, wax, or microparticle-based implants.

Therapeutic formulations of dor3, such as for promoting neural tissue growth or bone cell growth, may be prepared for storage by mixing dor3 having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed when administered, and include buffers such as phosphate, citrate, and other organic acids; antioxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Inventive complexes can comprise a ligand characterized by the inventive dor3 protein or fragment, which itself can be bound to a protein, such as antibody. Such antibodies can be polyclonal or monoclonal.

Polyclonal antibodies to dor3 generally are raised in animals by multiple subcutaneous (sc) or intraperitoneal (ip) injections of dor3 and an adjuvant. It may be useful to conjugate dor3 or a fragment containing the target amino acid sequence to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOcl_2$, or $R^1N=C=NR$.

Animals can be immunized against the immunogenic conjugates or derivatives by combining 1 mg or 1 μg of conjugate (for rabbits or mice, respectively) with 3 volumes of Freund's complete adjuvant and injecting the solution intradermally in multiple sites. One month later the animals are boosted with ⅕ to ¹⁄₁₀ the original amount of conjugate in Fruend's complete adjuvant by subcutaneous injection at multiple sites. Seven to 14 days later animals are bled and the serum is assayed for anti-dor3 titer. Animals are boosted until the titer plateaus. Preferably, the animal is boosted with the conjugate of the same dor3 polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

Dor3 antibodies are useful in diagnostic assays for dor3 or its antibodies. In one embodiment of a receptor binding assay, an antibody composition which binds to all of a selected plurality of members of the dor3 family is immobilized on an insoluble matrix, the test sample is contacted with the immobilized antibody composition in order to adsorb all dor3 family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

Dor3 antibodies also are useful for the affinity purification of dor3 from recombinant cell culture or natural sources. Dor3 antibodies that do not detectably cross-react with other growth factors can be used to purify dor3 free from these other family members.

Aspects of the invention will now be illustrated by the following examples.

EXPERIMENTAL PROCEDURES
Production of Xenopus Embryos

Xenopus embryos were prepared by the protocol described by Condie and Harland (*Development*, 101, 93–105, 1987). Embryos were staged according to the table of Nieuwkoop and Faber ("Normal Table of Xenopus laevis" (Daubin), Amsterdam: North Holland, 1967). Ventralized embryos were produced by UV irradiation with a Statalinker (Stratagene), and dorsalized embryos were produced by treatment with LiCl as described by us in our paper on certain "wnt" proteins (designated "Xwnt-8"), Smith and Harland, *Cell*, Vol. 67, pp. 753–765 (1991) (incorporated by reference and occasionally referred to hereinafter as "S&H, supra").

EXAMPLE 1
Isolation and Sequencing of Dor3 cDNA

The construction of the size-selected plasmid cDNA library from stage 11 LiCl-treated embryos was as follows. Sixty micrograms of poly(A)$^+$ RNA from stage 11 LiCl-treated embryos was size fractionated on a 10% to 30% sucrose gradient in the presence of methylmercuric hydroxide. First strand cDNA was synthesized from 2 $\mu$g of the size-fractionated poly(A)$^+$ RNAs primed with oligo(dT) oligonucleotide containing the recognition site for NotI. After synthesis of the second strand, cDNAs were treated with EcoRI methylase, ligated with EcoRI linkers, digested with EcoRI and NotI, and finally ligated to 125 ng of modified pGEM-5Zf(−) (Promega). The pGEM-5Zf(−) used here was modified by the addition of an oligonucleotide into the NsiI site to create an EcoRi site. The vector was not treated with alkaline phosphatase, but the excised polylinker sequence was removed on a sepharose 4BCL column. The ligated products were used to transform XL-I Blue cells (Stratagene), and plated to give 100,000 colonies per 15 cm plate. Plasmid DNAs were isolated form plate cultures by the alkaline-lysis/polyethylene glycol precipitation protocol.

Dorsalizing activity in the library was assayed by injecting RNA transcripts made from pooled plasmid DNA. Single clones were isolated by a process of sib selection. In this procedure the plasmid library was replated on 12 plates with 10-fold fewer colonies per plate. RNA was synthesized from pooled plasmid DNAs isolated from each plate and tested for dorsalizing activity by injection into UV-ventralized embryos. Those pools with dorsalizing activity were replated and screened as described above. This process was repeated until single clones were isolated.

In vitro RNA synthesis, injection assay for dorsal axis rescue and sib-selections were also done, as described by us in S&H, supra.

The nucleotide sequence of both strands of the isolated dor3 cDNA clone was determined by the dideoxy termination method using modified T7 DNA polymerase (US Biochem). Deletions were prepared in sequencing templates by both restriction enzyme and exonuclease III digestion (Henikoff, *Meth. Enzymol*, 155, 156–165, 1987).

RNA Isolation and Analysis

Total RNA was isolated from embryos and oocytes by a small scale protocol as described by Condie and Harland, supra. Dorsal lips were dissected from 30 unfixed stage 10.5 embryos and pooled for total RNA preparation. Samples containing either the total RNA equivalent of 2.5 embryos or approximately 2 $\mu$g of poly A+ RNA were analyzed by northern blotting. Random primed DNA probes were prepared from a 1,323 bp fragment of dor3 cDNA from the EcoRI site at nucleotide −83 to an EcoRV sites that lies in the vector immediately 3' to the end of the cDNA.

RNAse protection assays were done using a protocol as detailed by Melton et al. (*Nuc. Acids Res.*, 12, 7035–7056, 1984) with minor modifications (C. Kintner, Salk Institute, La Jolla, Calif.). A dor3 cDNA exonuclease III deletion clone, illustrated by SEQ ID NO:1 but having a deletion from the 3' end to nucleotide 383, was used as a template for synthesizing RNA probes. The template DNA was linearized by Eco RI restriction enzyme digestion and a 463 base antisense RNA incorporating $^{32}$P was synthesized with T7 RNA polymerase. A 387 base antisense EF1$\alpha$ RNA probe was used as a control for amount of RNA per sample. Probes were gel purified prior to use.

In situ Hybridization

After fixation and storage, the embryos were checked to ensure the blastocoel and archenteron were punctured. Care was taken to puncture the residual blastocoel of neurulae and tadpoles as well as the archenteron. Embryos were rewashed at room temperature in 100% ethanol for two hours to remove residual lipid. After hybridization, staining was allowed to develop overnight and the embryos were then fixed in Bouin's. Newly stained embryos have a high background of pink stain but most of this washes out, leaving the specific stain. Following overnight fixation, the embryos were washed well with 70% ethanol, 70% ethanol buffered with PBS and methanol. Embryos were cleared in Murray's mix and photographed with Kodak Ektar 25 film, using a Zeiss axioplan microscope (2.5 or 5× objective with 3×12B telescope to assist with focusing).

Dor3 CDNA Encodes a Novel Polypeptide

The coding strand of the 1634 nucleotide sequence of the selected clone is shown by SEQ ID NO:1. At the amino terminus of the expressed polypeptide, the hydrophobic stretch of amino acids suggests that the polypeptide enters the secretory pathway.

As earlier noted, comparison of the amino acid sequence of the predicted polypeptide to the National center for Biotechnology Information BLAST network (non-redundant data base) resulted in only a 33% overall identity to "nodal." Thus, this clone encodes the new type of protein we have named "dor3," which is secreted, and which has dorsal inducing activity in Xenopus. The predicted translated amino acid sequence is SEQ ID NO:3.

Dor3 MRNA can Rescue a Dorsal Structure

Injection of dor3 RNA into a single blastomere of a four cell stage UV-ventralized embryo can restore dorsal structures. The degree of axis rescue was dependent upon the amount of RNA injected, with embryos receiving low doses having only posterior dorsal structures, while embryos receiving higher doses had excess trunk tissue.

The rescue of dorsal development by both dor3 and Xwnt-8 mRNAs followed a consistent pattern in which increasing amounts of the mRNAs lead to progressively more anterior structures being rescued. However, whereas Xwnt-8 RNA can induce head formation, dor3 induces trunk formation (including spinal cord).

Dor3 mRNA is Expressed Zygotically

In northern blot analysis of RNA from Xenopus embryos one dor3 mRNA species of approximate size 1.8 kb was observed. No dor3 mRNA was detected in oocytes. Dor3 was expressed transiently during embryogenics, only during gastrulation.

We expect that the primary dorsalizing RNA in our library to be elevated in LiCl-treated embryos relative to normal or UV-treated embryos. Lithium ion treatment resulted in a very large increase in the amount of dor3 mRNA expressed, relative to untreated embryos. UV treatment had the opposite effect. Dor3 mRNA expression was essentially undetectable in total RNA samples from these embryos. Thus, the abundance of dor3 mRNA in manipulated embryos parallels the rescuing activity.

The localization of dor3 transcripts was investigated in early gastrula stage embryos. Dorsal lips were dissected from stage 10.5 embryos. A northern blot of equal amounts of total RNA from intact embryos, dissected dorsal lips, and from the remaining embryo after dissection of the dorsal lip was hybridized with a dor3 probe and then re-hybridized with an EF1α probe, as a control for amount of RNA loaded per sample. The autoradiograph of the blot showed that dor3 mRNA at this stage is enriched in the dorsal lip.

In situ Hybridization; Zygotic Expression of Dor3 in the Spemann Organizer

The localization of dor3 transcripts in developing embryos was examined in greater detail using whole mount in situ hybridization. Whole fixed embryos were hybridized with digoxigenin containing RNA probes. Hybridized RNA probe was then visualized with an alkaline phosphatase-conjugated anti-digoxigenin antibody. The specificity of hybridization seen with antisense dor3 probes was tested both by hybridizing embryos with sense dor3 probes, and by using two non-overlapping antisense probes. The increased level of dor3 mRNA that was detected by northern blot following activation of zygotic transcription was apparent in situ hybridization at stage 9 as a patch of staining cells on the dorsal side of the embryo. Viewed from the vegetal pole, this patch of cells was restricted to a sector of about 60°. A side view of the same embryo shows that the staining cells were located within the marginal zone (i.e., between the animal and vegetal poles and within the presumptive dorsal mesoderm forming region). Transcripts are largely restricted to the nucleus at this stage.

A side view of an early gastrula stage embryo (approximate stage 10.5) shows specific hybridization primarily in the involuting mesoderm at the dorsal lip. A vegetal view of the same embryo (blastopore lip arrowed) shows that dor3 mRNA is most abundant on the dorsal side, but expression extends at the lower level to the ventral side of the embryo. This method of in situ hybridization does not detect transcripts in the most yolky endodermal region of embryos, therefore we cannot rule out expression in more vegetal regions. Treatments which are known to affect the size of the dorsal lip (LiCl treatment, UV irradiation) had a profound effect on the pattern of dor3 in situ hybridization. In LiCl treated embryos the staining is intense throughout the marginal zone and animal pole ectoderm. UV treatment reduced the hybridization signal to low levels. This result in consistent with amounts of dor3 mRNA seen by northern blot analysis. The UV treated embryo also is a negative control for specificity of hybridization.

EXAMPLE 2

Mouse dor3 was isolated from a genomic library by probing with a radiolabelled frog dor3 cDNA under conditions of moderate stringency.

EXAMPLE 3

We have directed dor3 expression to gastrula stage animal caps by injecting the plasmid pCSKA-dor3 into the animal pole of a one cell stage embryo. The CSK-dor3 plasmid was constructed by standard methods, using the pCSKA vector and the dor-3 cDNA. Similar plasmid constructions have been described by Smith et al., Nature, 361 pp. 547–549 (1993). This plasmid, in which dor3 is under the control of the cytoskeletal actin promoter, turns on the expression of dor3 mRNA at the onset of gastrulation. At the blastula stage, the animal caps are dissected and then matured to tailbud stages for molecular analysis. Animal caps injected with the dor3 plasmid show expression of N-CAM in the absence of muscle or notochord markers. A control plasmid directing the expression of lac Z showed no neural or mesodermal induction as expected. Thus, it appears that dor3 can directly induce neural tissue in gastrula stage ectoderm, a stage when neural induction is taking place in whole embryos.

It is to be understood that while the invention has been described above in conjunction with preferred specific embodiments, the description and examples are intended to illustrate and not limit the scope of the invention, which is defined by the scope of the appended claims.

It is claimed:

1. An isolated oligonucleotide that encodes the polypeptide of SEQ ID NO:3.

2. An oligonucleotide that is complementary to the oligonucleotide of claim 1, as depicted in SEQ ID NO: 2.

3. An expression vector comprising a nucleotide sequence that encodes the polypeptide of SEQ ID NO:3.

4. An isolated mammalian, bacterial, or insect host cell that contains the expression vector of claim 3, and produces the polypeptide of SEQ ID NO: 3.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1644 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Xenopus laevis
      (D) DEVELOPMENTAL STAGE: Embryo (xi) SEQUENCE DESCRIPTION: SEQ ID NO:1:

```
CCATACCATA GTCTGAACAA GAAGCATCTC CTCAGTTGGA AGATATCTGG AGTCACCACA        60
```

```
AATCTACCCA GAGATGGCAT TTCTGAACCT GTTCTTCTGC CTTGTGTTTA TCTCCCCACT      120

GATGGCGATG CCTCCAGTCC TACAGGGGAG AAAGTCCATC AGTCCAGATT CTATCCTAAA      180

GGACACATCC ACAGATATTG GAGCCAGAGA ATTTCAAGGA AGGAAGTTCC CCAATTTTAT      240

GATGCAGCTG TACCAGAATA TCATCAGAGG TAGAGATAAT GATCTATCCA ACCTGGAACA      300

TCCTACTCTT CAGGAATCTG ATACCGTCCA AAGCTTCATC GCTAAAAGTT ATACTACAGT      360

GGGGAATCGC TGGACCTTGT TCTTTGATAT GTCCTCCATC TCTAGAAGCA ACGAGCTGAA      420

GTTGGCTGAG CTACGTATTT GCCTCCCTTC TTTTAGAAAG TCTCACAGTG TGACAGTAGA      480

CATCTACCAT ACCAATGACG GCAAGGAGAA ATTATTCATG GGATCATTTA AGACCAAGCT      540

TTCTTCTGCA CTAGATTCTG ACTGCAAGGT CTTCAATCTC ACCATCTTGT TGCAGAACTT      600

TCTGACCAGG GGAAAGAGGT TAATAAAGGA TGAATACATA CAGGCAAAAG GTCTCCATCT      660

GAAAGATCTA GAGAAGAGTG CTACAGAAAA AGATACAGAA AATGTAGATA CGATGAAGCA      720

ACATCAATAT CACGTATCTG ACTTTGCTGC AGAAAGAATA ATGCTGGTTG TGTTTGCTAA      780

AGAACAGTCT CATGCTAAAC CTGATCCCCC CAGTCTTGGC CAGAAGCTGT TCCCTTCAAA      840

GTATGGTATT GATGATAATG CCAACAAGGT GAATGGATTT CGGAGACTTA GAAGGAACAA      900

GAAAGAGAAA ACACAAATCC ATGTGAGCAC CGTTCCACCT AAACCTATTG AAGAGATCAA      960

ACCCGAGTGC AAGAAGGTGG ACATGTTTGT GGACTTTCAG AAGATCGGAT GGGGCAGCTG     1020

GATTATTTAT CCCAAGGCAT ATAATGCATA TAGATGTGAA TCCACTTGTG CAGTTCCACA     1080

GAATGAGACA GAGAATGCAA CAAACCATTC CTACATTAAG AGTTTGCTCC CTCTGAGTGA     1140

CATGGAGAGA AAAGAGTGTC CCTCCTGTGT CCCCATGAAG ATGATGTCCA TGTCAATGTT     1200

GTACTATGAG AATGAAGATT TTATCCTGAG GCACCATGAA GAGATGATTG TAGAAGAATG     1260

TGGATTCAAG GACATGTAAC ACAGACTGTC TCCTAAACTT TTTTTACTAC ATCCAACTAA     1320

CTACATCGTT TCTTGGATTC CTTATTTATG CCATGTTTTT AACATTACTG TTTTAGGCAC     1380

ATATTTATCT TTTGTTTTTT AGATTGATT  TTTAATCTGT TGTGCCGATC CATGGATCCA     1440

CATTTTACAG AGCAGCACTT CTTGTCCCAC TATTTATTGT GCACATGAGA TTGGCTCTGT     1500

TTTCCAGTTA AAGCTATATT TTGTGCAATG TTTTATATTT TTTATGAAAA AGGGCAACAT     1560

TGATATACAA TGTAGATATT AATTCTAACA TGGAATATCG TGATAGATTT GAATAAAAAT     1620

GTTCAGCTAA AAAAAAAAAA AAAA                                           1644
```

(2) INFORMATION FOR SEQ ID NO:2:

(i) SEQUENCE CHARACTERISTICS:
        (A) LENGTH: 1644 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Xenopus laevis
        (D) DEVELOPMENTAL STAGE: Embryo (xi) SEQUENCE DESCRIPTION: SEQ ID NO:2:

```
CCATACCATA TTTTTTTTTT TTTTTTAGCT GAACATTTTT ATTCAAATCT ATCACGATAT       60

TCCATGTTAG AATTAATATC TACATTGTAT ATCAATGTTG CCCTTTTTCA TAAAAAATAT      120
```

-continued

```
AAAACATTGC ACAAAATATA GCTTTAACTG GAAAACAGAG CCAATCTCAT GTGCACAATA      180

AATAGTGGGA CAAGAAGTGC TGCTCTGTAA AATGTGGATC CATGGATCGG CACAACAGAT      240

TAAAAATCAA ATCTAAAAAA CAAAAGATAA ATATGTGCCT AAAACAGTAA TGTTAAAAAC      300

ATGGCATAAA TAAGGAATCC AAGAAACGAT GTAGTTAGTT GGATGTAGTA AAAAAAGTTT      360

AGGAGACAGT CTGTGTTACA TGTCCTTGAA TCCACATTCT TCTACAATCA TCTCTTCATG      420

GTGCCTCAGG ATAAAATCTT CATTCTCATA GTACAACATT GACATGGACA TCATCTTCAT      480

GGGGACACAG GAGGGACACT CTTTTCTCTC CATGTCACTC AGAGGGAGCA AACTCTTAAT      540

GTAGGAATGG TTTGTTGCAT TCTCTGTCTC ATTCTGTGGA ACTGCACAAG TGGATTCACA      600

TCTATATGCA TTATATGCCT TGGGATAAAT AATCCAGCTG CCCCATCCGA TCTTCTGAAA      660

GTCCACAAAC ATGTCCACCT TCTTGCACTC GGGTTTGATC TCTTCAATAG GTTTAGGTGG      720

AACGGTGCTC ACATGGATTT GTGTTTTCTC TTTCTTGTTC CTTCTAAGTC TCCGAAATCC      780

ATTCACCTTG TTGGCATTAT CATCAATACC ATACTTTGAA GGGAACAGCT TCTGGCCAAG      840

ACTGGGGGGA TCAGGTTTAG CATGAGACTG TTCTTTAGCA AACACAACCA GCATTATTCT      900

TTCTGCAGCA AAGTCAGATA CGTGATATTG ATGTTGCTTC ATCGTATCTA CATTTTCTGT      960

ATCTTTTTCT GTAGCACTCT TCTCTAGATC TTTCAGATGG AGACCTTTTG CCTGTATGTA     1020

TTCATCCTTT ATTAACCTCT TTCCCCTGGT CAGAAAGTTC TGCAACAAGA TGGTGAGATT     1080

GAAGACCTTG CAGTCAGAAT CTAGTGCAGA AGAAAGCTTG GTCTTAAATG ATCCCATGAA     1140

TAATTTCTCC TTGCCGTCAT TGGTATGGTA GATGTCTACT GTCACACTGT GAGACTTTCT     1200

AAAAGAAGGG AGGCAAATAC GTAGCTCAGC CAACTTCAGC TCGTTGCTTC TAGAGATGGA     1260

GGACATATCA AGAACAAGG TCCAGCGATT CCCCACTGTA GTATAACTTT TAGCGATGAA     1320

GCTTTGGACG GTATCAGATT CCTGAAGAGT AGGATGTTCC AGGTTGGATA GATCATTATC     1380

TCTACCTCTG ATGATATTCT GGTACAGCTG CATCATAAAA TTGGGAACT TCCTTCCTTG     1440

AAATTCTCTG GCTCCAATAT CTGTGGATGT GTCCTTTAGG ATAGAATCTG GACTGATGGA     1500

CTTTCTCCCC TGTAGGACTG GAGGCATCGC CATCAGTGGG GAGATAAACA CAAGGCAGAA     1560

GAACAGGTTC AGAAATGCCA TCTCTGGGTA GATTTGTGGT GACTCCAGAT ATCTTCCAAC     1620

TGAGGAGATG CTTCTTGTTC AGAC                                           1644
```

(2) INFORMATION FOR SEQ ID NO:3:

(i) SEQUENCE CHARACTERISTICS:
        (A) LENGTH: 401 amino acids
        (B) TYPE: amino acid
        (D) TOPOLOGY: unknown (ii) MOLECULE TYPE: protein (iii) HYPOTHETICAL: YES (xi) SEQUENCE DESCRIPTION: SEQ ID NO:3:

```
Met Ala Phe Leu Asn Leu Phe Phe Cys Leu Val Phe Ile Ser Pro Leu
1               5                   10                  15

Met Ala Met Pro Pro Val Leu Gln Gly Arg Lys Ser Ile Ser Pro Asp
            20                  25                  30

Ser Ile Leu Lys Asp Thr Ser Thr Asp Ile Gly Ala Arg Glu Phe Gln
        35                  40                  45

Gly Arg Lys Phe Pro Asn Phe Met Met Gln Leu Tyr Gln Asn Ile Ile
    50                  55                  60

Arg Gly Arg Asp Asn Asp Leu Ser Asn Leu Glu His Pro Thr Leu Gln
65                  70                  75                  80
```

-continued

```
Glu Ser Asp Thr Val Gln Ser Phe Ile Ala Lys Ser Tyr Thr Thr Val
                85              90              95

Gly Asn Arg Trp Thr Leu Phe Phe Asp Met Ser Ser Ile Ser Arg Ser
            100             105             110

Asn Glu Leu Lys Leu Ala Glu Leu Arg Ile Cys Leu Pro Ser Phe Arg
        115             120             125

Lys Ser His Ser Val Thr Val Asp Ile Tyr His Thr Asn Asp Gly Lys
    130             135             140

Glu Lys Leu Phe Met Gly Ser Phe Lys Thr Lys Leu Ser Ser Ala Leu
145             150             155             160

Asp Ser Asp Cys Lys Val Phe Asn Leu Thr Ile Leu Leu Gln Asn Phe
            165             170             175

Leu Thr Arg Gly Lys Arg Leu Ile Lys Asp Glu Tyr Ile Gln Ala Lys
            180             185             190

Gly Leu His Leu Lys Asp Leu Glu Lys Ser Ala Thr Glu Lys Asp Thr
            195             200             205

Glu Asn Val Asp Thr Met Lys Gln His Gln Tyr His Val Ser Asp Phe
210             215             220

Ala Ala Glu Arg Ile Met Leu Val Val Phe Ala Lys Glu Gln Ser His
225             230             235             240

Ala Lys Pro Asp Pro Pro Ser Leu Gly Gln Lys Leu Phe Pro Ser Lys
            245             250             255

Tyr Gly Ile Asp Asp Asn Ala Asn Lys Val Asn Gly Phe Arg Arg Leu
            260             265             270

Arg Arg Asn Lys Lys Glu Lys Thr Gln Ile His Val Ser Thr Val Pro
            275             280             285

Pro Lys Pro Ile Glu Glu Ile Lys Pro Glu Cys Lys Lys Val Asp Met
    290             295             300

Phe Val Asp Phe Gln Lys Ile Gly Trp Gly Ser Trp Ile Ile Tyr Pro
305             310             315             320

Lys Ala Tyr Asn Ala Tyr Arg Cys Glu Ser Thr Cys Ala Val Pro Gln
            325             330             335

Asn Glu Thr Glu Asn Ala Thr Asn His Ser Tyr Ile Lys Ser Leu Leu
            340             345             350

Pro Leu Ser Asp Met Glu Arg Lys Glu Cys Pro Ser Cys Val Pro Met
        355             360             365

Lys Met Met Ser Met Ser Met Leu Tyr Tyr Glu Asn Glu Asp Phe Ile
    370             375             380

Leu Arg His His Glu Glu Met Ile Val Glu Glu Cys Gly Phe Lys Asp
385             390             395             400

Met
```